United States Patent [19]

Chapman et al.

[11] 4,249,030

[45] Feb. 3, 1981

[54] ALKYLATION PROCESS

[75] Inventors: Charles C. Chapman; Paul D. Hann, both of Bartlesville, Okla.

[73] Assignee: Phillips Petroleum Company, Bartlesville, Okla.

[21] Appl. No.: 63,006

[22] Filed: Aug. 2, 1979

[51] Int. Cl.³ .............................. C07C 2/56; F28D 7/00
[52] U.S. Cl. .................................. 585/716; 422/235; 585/717; 585/719; 585/723
[58] Field of Search ............... 585/717, 711, 716, 719, 585/723; 422/235

[56] References Cited

U.S. PATENT DOCUMENTS

| | | | |
|---|---|---|---|
| 2,342,677 | 2/1944 | Linn | 585/717 |
| 3,113,987 | 12/1963 | Hutson, Jr. | 585/719 |
| 3,158,661 | 11/1964 | Plaster et al. | 585/719 |
| 3,763,266 | 10/1973 | Henderson | 585/716 |
| 4,008,292 | 2/1977 | James | 585/719 |
| 4,059,649 | 11/1977 | Chapman et al. | 585/719 |
| 4,112,010 | 9/1978 | Dixon | 585/719 |
| 4,144,281 | 3/1979 | Chapman et al. | 585/719 |

*Primary Examiner*—Curtis R. Davis

[57] ABSTRACT

Propylene and butylenes are separately acid alkylated with at least one isoparaffin. Expansion and liquid-vapor separation is utilized to separate the propylene from the butylenes. The use of expansion and separation improves the energy efficiency of the alkylation process. The energy efficiency of the alkylation process is further improved by utilizing the bottoms product from the acid stripper associated with the isostripper to cool the acid being supplied to the riser reactor. The size requirements of the isostripper are also reduced by using liquid-vapor separation to remove at least a portion of the unreacted isoparaffin from the alkylated butylenes.

21 Claims, 3 Drawing Figures

ALKYLATION PROCESS

This invention relates to an improved, energy efficient alkylation process and an apparatus suitable for carrying out said process. In one aspect, this invention relates to an alkylation process in which at least one isoparaffin is separately added to propylene and to butylenes. In another aspect, this invention relates to an alkylation process in which expansion and liquid-vapor separation is utilized to separate the propylene from the butylenes. In another aspect, this invention relates to an alkylation process in which the bottoms product from the acid stripper associated with the isostripper is flashed and utilized to cool the acid catalyst being supplied to the riser reactor. In another aspect this invention relates to an alkylation process in which liquid vapor separation is utilized to reduce the concentration of any unreacted isoparaffin in the bottoms product from the acid stripper associated with the isostripper to thereby allow a substantial reduction in the size and cost of the isostripper.

Alkylation is a process to combine at least one isoparaffin such as isobutane with an olefin such as propylene, butylenes or amylenes to produce a liquid with superior stability and antiknock quality suitable for blending aviation gasoline and motor fuel. An acid catalyst such as hydrofluoric (HF) acid or sulfuric acid serves to catalyze the reaction.

The isoparaffin commonly alkylated is isobutane although isopentane could be utilized if desired. The most commonly used olefins are propylene and butylenes which amylenes being used less frequently. As used herein the term butylenes refers to 1-butene, cis-2-butene, trans-2-butene and isobutylene. As used herein the term amylenes refers to all of the five carbon olefins. Some propane and normal butane may also be present with the propylene and butylenes, and some propane may be produced in the alkylation.

The present invention is described in terms of the separate alkylations of isobutane with propylene and isobutane with butylenes in the presence of hydrofluoric acid. However, the invention is not limited to this particular alkylation. Isopentane could be utilized as the isoparaffin if desired. Amylenes could be utilized as the olefin if desired. An acid such as sulfuric acid could be utilized as the acid catalyst if desired.

It is well known that the alkylation process is temperature sensitive. The temperature at which the alkylation process is carried out directly affects the octane value of the alkylate produced. However, a somewhat higher temperature is desirable when the isobutane is alkylated with propylene than when the isobutane is alkylated with butylenes. Where the feedstream contains a mixture of propylene and butylenes and generally some propane and normal butane, it is desirable to separate the propylene and propane from the butylenes and normal butane. In the past, this separation has commonly been accomplished by the use of a fractionator. However, a fractionation process requires considerable bottoms reboiling heat and overhead cooling. The reaction effluent comprising butylenes and normal butane flowing from the fractionator is generally too hot to be utilized in the alkylation process. The reaction effluent must thus be cooled. The required heating in the fractionator and the required cooling result in considerable energy expenditures which are undesirable in a commercial process. It is thus an object of this invention to provide method and apparatus for utilizing expansion and liquid-vapor separation to separate the propylene and propane from the butylene and normal butane. This results in a considerable reduction in energy cost for the alkylation process.

A major expense in the alkylation process is the isostripper. The size (diameter and wall thickness) and thus the expense of the isostripper can be considerably reduced if the concentration of any unreacted isobutane can be reduced in the feed flowing to the stripper, and with this feed being HF-free. It is thus an object of this invention to provide method and apparatus for utilizing liquid-vapor separation to reduce the concentration of any unreacted isoparaffin in the bottoms product from the acid stripper associated with the isostripper to thereby allow a substantial reduction in the size and cost of the isostripper.

Other streams in the process are also utilized to improve the energy efficiency of the alkylation process. In particular, the bottoms product from the acid stripper associated with the isostripper is flashed and is utilized to cool the acid which is being supplied to the riser reactor. In this manner, the temperature at which the butylenes alkylation process is carried out is reduced which results in a higher octane value for the alkylate produced. It is thus an object of this invention to provide method and apparatus for flashing the bottoms product from the acid stripper associated with the isostripper and utilizing the thus cooled bottoms product from the acid stripper to cool the acid being supplied to the riser reactor.

Other process streams are also utilized to improve the energy efficiency of the alkylation process. These process streams will be particularly pointed out in the detailed description of the invention. Also, a particular type of liquid-vapor separator can be utilized to improve the separation of the propylene and propane from the butylene and normal butane. Also, hydrofluorination of the bottoms product from the liquid-vapor separator can be utilized to improve the alkylation process.

In accordance with the present invention, method and apparatus is provided whereby a feed comprising propylene, propane, isobutane, butylenes, normal butane and recycled isobutane is expanded and provided to a first liquid-vapor separator. The propylene and propane and some isobutane is separated as a vapor from the butylene, normal butane and remaining isobutane which was not vaporized. The propylene, propane and vaporized isobutane is provided as an overhead product from the first liquid-vapor separator to an alkylation process in which isobutane is alkylated with propylene in a first riser reactor. The butylenes, normal butane and isobutane, which remains in liquid form, is provided as a bottoms product to a second riser reactor in which the isobutane is alkylated with the butylenes in the presence of hydrofluoric acid.

The bottoms product from the acid stripper associated with the isostripper is expanded and is utilized to cool the hydrofluoric acid being supplied to the second riser reactor. The bottoms product from the acid stripper associated with the isostripper is provided after expansion to a second liquid-vapor separator. The overhead from the second liquid-vapor separator is supplied to the alkylation process for the propylene and isobutane. The bottoms product from the second liquid-vapor separator is supplied as a feed to the isostripper.

Heat exchange between other process streams is also utilized to improve the energy efficiency of the alkylation process. Hydrofluorination of the bottoms product from the first liquid-vapor separator is utilized, if desired, to improve the alkylation process. Trays are utilized in the first liquid-vapor separator, if desired, to improve the separation of the propylene and propane from the butylenes and normal butane.

Other objects and advantages of the invention will be apparent from the foregoing brief description of the invention and the claims as well as from the detailed description of the drawings in which:

The alkylation process of the present invention is described in terms of a particular process configuration. However, the invention is applicable to different process configurations which accomplish the purpose of the present invention. Different combinations of process streams may be used for heating and cooling if desired and still be within the scope of the present invention.

Figure 1:
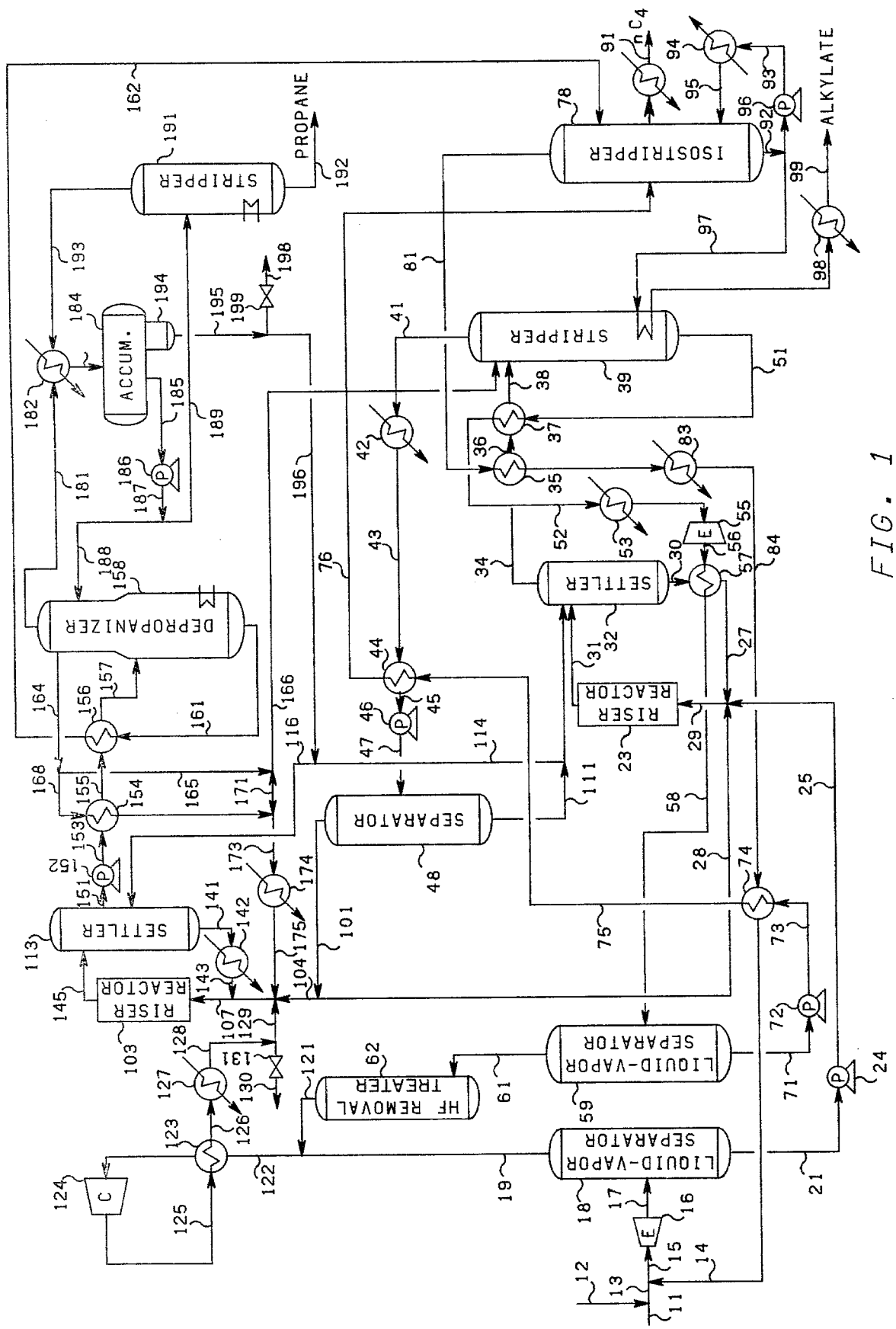
FIG. 1 is a diagrammatic illustration of an alkylation process.

Referring now to the drawings, and in particular to FIG. 1, a feed which preferably comprises propylene and butylenes, with some propane, normal butane and isobutane also being present, is provided through conduit means 11. The feed flowing through conduit means 11 is combined with an isobutane feed flowing through conduit means 12. The combined feed is provided through conduit means 13. The combined feed flowing through conduit means 13 is combined with recycle isobutane flowing through conduit means 14. The total combined feed is provided through conduit means 15 to the expander 16. The total combined feed is expanded and provided through conduit means 17 to the liquid-vapor separator 18. A vapor rich in propylene and propane and also containing some isobutane is removed as an overhead product from the liquid-vapor separator 18 through conduit means 19. A chilled liquid enriched in butylenes, isobutane and normal butane is removed as a bottoms product through conduit means 21 from the liquid-vapor separator 18. The bottoms product is pumped from conduit means 21 into conduit means 25 through pumping means 24. The bottoms product from the liquid-vapor separator 18 is combined with hydrofluoric acid flowing through conduit means 27 and isobutane flowing through conduit means 28. The combined stream is provided through conduit means 29 to the riser reactor 23. The liquid product from the riser reactor 23, which will generally comprise unreacted isobutane, butylenes alkylate, normal butane and hydrofluoric acid is provided through conduit means 31 to the settler 32. The hydrofluoric acid is phase separated from the unreacted isobutane, the butylenes alkylate and the normal butane in the settler 32 and is provided as a bottoms product through conduit means 30, heat exchanger 57 and conduit means 27 to the riser reactor 23 as has previously been described. The unreacted isobutane and the butylenes alkylate along with the charged normal butane and dissolved and entrained HF is removed as an overhead product from the settler 32 through conduit means 34. The overhead product is provided through conduit means 34, heat exchanger 35, conduit means 36, heat exchanger 37, and conduit means 38 to the stripper 39. Hydrofluoric acid and a portion of the isobutane is stripped from the overhead product flowing from the settler 32 into stripper 39. The stripped hydrofluoric acid and isobutane vapors are provided as an overhead product through conduit means 41, heat exchanger 42, conduit means 43, heat exchanger 44, conduit means 45, pumping means 46 and conduit means 47 to the separator 48. The butylenes alkylate, normal butane and and remaining isobutane is withdrawn from the stripper 39 as a bottoms product through conduit means 51. The bottoms product from the stripper 39 is provided through the combination of conduit means 51, heat exchanger 37, conduit means 52, heat exchanger 53, conduit means 54, expander 55, conduit means 56, heat exchanger 57, and conduit means 58 to the liquid-vapor separator 59.

At least a portion of the isobutane in the stream charged to the liquid-vapor separator 59 is separated as an overhead vapor product through conduit means 61 and is provided to the HF removal treater 62. The bottoms product from the liquid-vapor separator which will consist essentially of the butylenes alkylate, normal butane, a small concentration of isobutane but freed of hydrofluoric acid is withdrawn as a bottoms product from the liquid-vapor separator 59 through conduit means 71. The bottoms product from the liqid-vapor separator 59 is provided through the combination of conduit means 71, pumping means 72, conduit means 73, heat exchanger 74, conduit means 75, heat exchanger 44, and conduit means 76 to the isostripper 78. Isobutane is stripped from the feed charged through conduit means 76 and the feed charged through conduit means 162 in the isostripper 78 and is withdrawn as an overhead product through conduit means 81. The thus stripped isobutane is recycled through the combination of conduit means 81, heat exchanger 35, conduit means 82, heat exchanger 83, conduit means 84, heat exchanger 74, conduit means 14 and conduit means 15 to the expander 16. Normal butane is removed from the isostripper through conduit means 91. Butylenes alkylate and propylene alkylate blend is removed as a bottoms product from the isostripper 78 through conduit means 92. The thus withdrawn alkylate blend is recycled in part to the isostripper 78 through pumping means 96, conduit means 93, heat exchanger 94 and conduit means 95 as stripping fluid. The alkylate is also provided to the reboiler of the stripper 39 through conduit means 97. After reboiling the stripper 39, the alkylate is passed through heat exchanger 98 and is withdrawn as an alkylate product through conduit means 99.

The hydrofluoric acid and isobutane, which are charged to the separator 48, are liquid phase separated. The isobutane is provided as an overhead product through conduit means 101. The isobutane is provided to the riser reactor 23 through the combination of conduit means 101, 28 and 29. The isobutane is provided to the riser reactor 103 through the combination of conduit means 101, conduit means 104, conduit means 105 and conduit means 107. The hydrofluoric acid is provided as a bottoms product from the separator 48 through conduit means 111. The hydrofluoric acid is provided to the settler 32 through the combination of conduit means 111 and conduit means 112. The hydrofluoric acid acid is provided to the settler 113 through the combination of conduit means 111, conduit means 114 and conduit means 116.

The HF removal treater 62 is preferably filled with a solid bed of particles or chips of potassium hydroxide.

The isobutane flowing through conduit means 61, which usually will contain trace amounts of hydrofluoric acid, is passed through the HF removal treater 62 to remove any hydrofluoric acid. A hydrofluoric acid free isobutane stream is provided through conduit means 121 from the HF removal treater 62. The isobutane stream flowing through conduit means 121 is combined with the overhead stream flowing through conduit means 19 from the liquid vapor separator 18 and is provided through the combination of conduit means 122, heat exchanger 123, compressor 124, conduit means 125, heat exchanger 123, conduit means 126, heat exchanger 127, conduit means 128, conduit means 129, conduit means 105 and conduit means 107 to the riser reactor 103.

The stream flowing through conduit means 128 may also be provided to another part of the alkylation process through conduit means 130 by opening control valve 131. The use of this stream flowing through conduit means 130 will be described hereinafter.

Hydrofluoric acid liquid is provided from the settler 113 as a bottoms product flowing through the combination of conduit means 141, heat exchanger 142, conduit means 143 and conduit means 107 to the riser reactor 103. The liquid reaction effluent from the riser reactor 103 which will comprise the propylene alkylate, unreacted isobutane, propane, and hydrofluoric acid is removed from the riser reactor 103 through conduit means 145 and is provided as a feed to the settler 113. The hydrofluoric acid is phase separated from the propylene alkylate, unreacted isobutane and propane and is withdrawn as a bottoms product from the settler 113 as has been previously described. The propylene alkylate, unreacted isobutane, dissolved and entrained HF, and propane product is withdrawn from the settler 113 through conduit means 151. The product flowing through conduit means 151 is provided through the combination of pumping means 152, conduit means 153, heat exchanger 154, conduit means 155, heat exchanger 156, and conduit means 157 as a feed to the depropanizer 158.

Propane and at least some isobutane are separated from the propylene alkylate in the depropanizer 158. The propylene alkylate containing some isobutane is provided as a bottoms product from the depropanizer 158 through conduit means 161. The propylene alkylate is provided through the combination of conduit means 161, heat exchanger 156 and conduit means 162 as a feed to the isostripper 78. The propylene alkylate containing some isobutane is treated in the isostripper as has been previously described.

An isobutane-rich stream is withdrawn as a side draw from the depropanizer 158 through conduit means 164. The thus withdrawn isobutane-rich stream is provided through the combination of conduit means 164, conduit means 165, and conduit means 166 to the stripper 39. The isobutane-rich stream is also provided through the combination of conduit means 164, conduit means 168, heat exchanger 154, conduit means 169, conduit means 171 and conduit means 166 to the stripper 39. The isobutane-rich stream flowing through conduit means 164 is also provided through the combination of conduit means 164, conduit means 165, conduit means 171, conduit means 173, heat exchanger 174, conduit means 175, conduit means 105 and conduit means 107 as recycle isobutane to the riser reactor 103. The isobutane-rich stream is also provided through the combination of conduit means 164, conduit means 168, heat exchanger 154, conduit means 169, conduit means 173, conduit means 174, conduit means 175, conduit means 105 and conduit means 107 as recycle isobutane to the riser reactor 103.

Propane and hydrofluoric acid vapor stream is withdrawn as an overhead product from the depropanizer 158 through conduit means 181. The propane and hydrofluoric acid are cooled and condensed in heat exchanger 182 and are provided through conduit means 183 to the accumulator-liquid phase separator 184. Liquid propane and dissolved and entrained hydrofluoric acid are withdrawn through conduit means 185. The liquid propane and hydrofluoric acid are provided through the combination of pumping means 186, conduit means 187 and conduit means 188 as a reflux to the depropanizer 158. The liquid propane and hydrofluoric acid are also provided through the combination of pumping means 186, conduit means 187 and conduit means 189 to the HF stripper 191. A substantially pure propane stream is withdrawn as a bottoms product from the stripper 191 through conduit means 192. An overhead stream containing hydrofluoric acid and propane is withdrawn from the stripper 191 through conduit means 193 and is recycled through heat exchanger 182 and conduit means 183 to the accumulator 184.

Substantially pure hydrofluoric acid is withdrawn from the leg 194 of the accumulator 184 and is provided through the combination of conduit means 195, 196, and 116 to the settler 113. The hydrofluoric acid may also be withdrawn through conduit means 198 by opening control valve 199 and utilized as described hereinafter.

The principle inventive feature of the present invention resides in the use of the liquid-vapor separators 18 and 59. Liquid-vapor separator 18 enables the propylene to be split from the butylenes at a relatively cool temperature. The butylenes can then be used to alkylate isobutane at a low temperature, with the propylene being used to alkylate isobutane at a somewhat higher temperature. The energy required for fractionation is eliminated and cooler process conditions are obtained for the butylenes alkylation (and for hydrofluorination).

The liquid vapor separator 59 separates at least some of the unreacted isobutane from the butylenes alkylate before the butylenes alkylate is provided to the isostripper 78. This allows the size of the isostripper to be reduced which results in substantial savings for the alkylation process.

A further inventive feature of the present invention is the manner in which the energy of the various process streams is utilized to cool or heat other process streams. In particular, the relatively high pressure of the bottoms product withdrawn from stripper 39 is utilized to cool the hydrofluoric acid flowing from the settler 32. This is accomplished by expanding or flashing a portion of the bottoms product from the stripper 39 in the expander 55 to reduce the temperature and thus provide a cooling stream for the indirect heat exchanger 57.

The following example is presented to more fully illustrate the present invention.

EXAMPLE

Using the process of the invention as illustrated in FIG. 1, the following flow rates and the following operating conditions for the alkylation process were calculated:

I. Operating Conditions

| Vessel | Pressure psia | Temperature Top | Temperature Bottom |
|---|---|---|---|
| (A) Liquid-vapor separator 18 | 40 | | 40 |
| (B) Liquid-vapor separator 59 | 40 | | 65 |
| (C) HF alkylation 23 and settler 32 | 150 | | 85 |
| (D) HF stripper 39 | 125 | 120 | 160 |
| (E) Isostripper 78 | 130 | 140 | 325 |
| (F) HF alkylation 103 and settler 113 | 110 | | 100 |
| (G) Depropanizer 158 | 300 | 120 | 250 |
| (H) HF stripper 191 | 330 | 120 | 140 |
| (I) Accumulator 184 | 160 | | 100 |
| (K) Expander 55 upstream pressure, 120 psia downstream pressure, 40 psia upstream temperature, 125° F. downstream (after exchanger), 70° F. | | | |

| Flow Rates | Barrels/Hour |
|---|---|
| Feed Olefins (conduit means 11) | 100 |

| Composition | Vol. % |
|---|---|
| Propylene | 21 |
| Propane | 14 |
| Butylenes | 30 |
| Isobutane | 25 |
| n-Butane | 10 |

| | Barrels/Hour |
|---|---|
| Feed Isobutane (conduit means 12) | 35 |
| Recycle Isobutane (conduit means 14) | 250 |
| Flash Vapor (measured as liquid) (HF-free) (conduit means 19) | 45 |
| Bottoms (conduit means 21) | 280 |
| Total Hydrocarbon to Butylenes Alkylation | 340 |

| Components | Vol. % |
|---|---|
| Butylenes | 9 |
| Isobutane | 88 |
| n-Butane | 3 |

| | |
|---|---|
| Isobutane/olefin vol. ratio in butylenes alkylation | 10/1 |
| Hydrofluoric acid/hydrocarbon liquid ratio in butylenes alkylation | 4/1 |
| HF Stripper Bottoms (conduit means 51) | 283 |
| HF Stripper Overhead, (measured as liquid), (HF not included in numeral) (conduit means 41) | 50 |
| Flashed vapor from liquid-vapor separator 59 (measured as liquid) (conduit means 61) | 20 |
| Total to Compressor 124, (measured as liquid) | 65 |
| Feed to Isostripper (conduit means 76) | 263 |
| Total Hydrocarbon to Propylene Alkylation | 255 |

| Components | Vol. % |
|---|---|
| Propylene | 8 |
| Propane | 6 |
| Isobutane | 86 |

| | |
|---|---|
| Isobutane/olefin vol. ratio in propylene alkylation | 10/1 |
| Hydrofluoric acid/hydrocarbon vol. ratio in propylene alkylation | 4/1 |
| Depropanizer 158 Bottoms | 67 |
| Normal Butane (conduit means 91) | 10 |
| Total Alkylate (conduit means 99) | 90 |
| Propane yield (conduit means 192) | 14 |
| Sidedraw (conduit means 164) | 150 |

Using the process shown in FIG. 1 and the flow rates and operating conditions specified in the example, an improved alkylation process is provided by the reduced temperature at which the butylenes alkylation is carried out and also by the reduced size of the isostripper 78.

Figure 2:
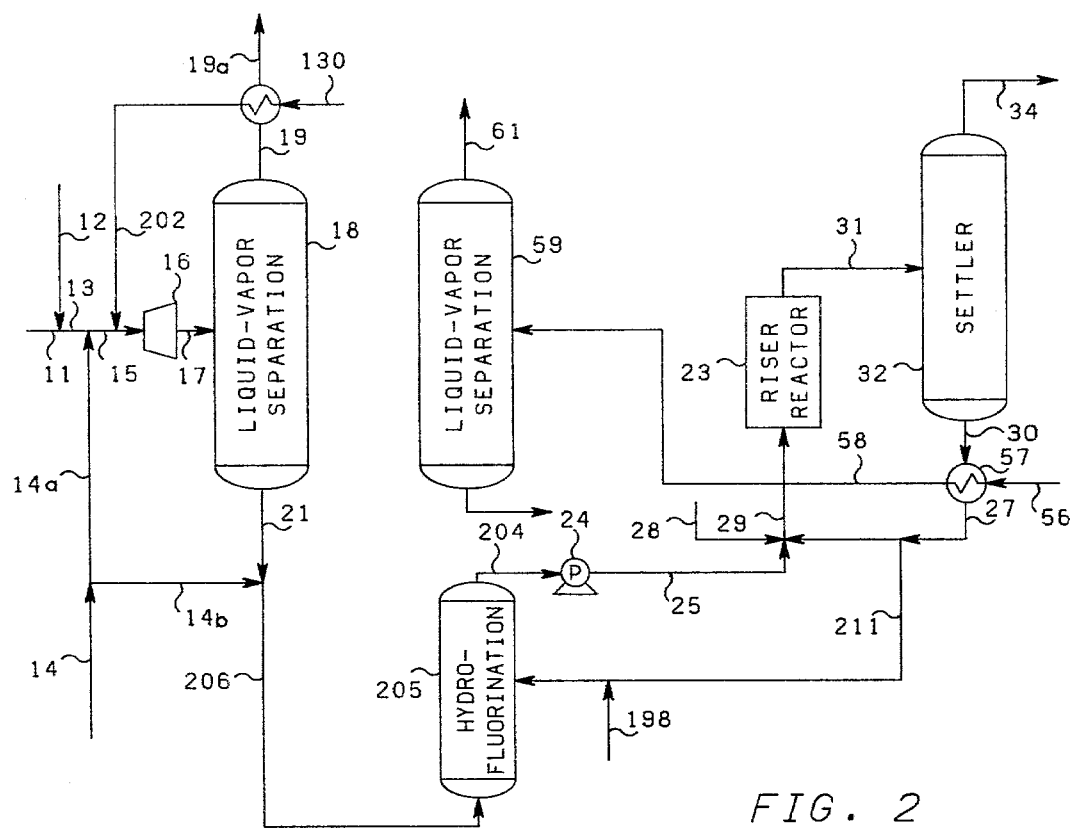
FIG. 2 is a diagrammatic illustration of a variation for the alkylation process illustrated in FIG. 1 in which hydrofluorination is incorporated.

FIG. 2 illustrates a variation for the alkylation process illustrated in FIG. 1 which can be utilized if desired. The principle feature illustrated in FIG. 2 is the hydrofluorination of the butylenes to produce butylfluorides which are used to alkylate isobutane in the riser reactor 23. Instead of being supplied directly to the pumping means 24, the bottoms product from the liquid-vapor separator 18 is provided by the combination of conduit means 21 and 206 to the hydrofluorination reactor 205. Recycle isobutane is also provided through the combination of conduit means 14, 14b and 206 to the hydrofluorination reactor 205. Hydrofluoric acid is provided to the hydrofluorination reactor 205 through conduit means 30, heat exchanger 57, conduit means 27 and conduit means 211. Hydrofluoric acid may also be added through conduit means 198 (see FIG. 1) if desired. The butylfluorides are provided from the hydrofluorination reactor 205 to the riser reactor 23 through the combination of conduit means 204, pumping means 24, conduit means 25, and conduit means 29.

The other variation illustrated in FIG. 2 is the use of a portion of the stream flowing through conduit means 130 (see also FIG. 1) as a recycle stream via exchanger 201 and conduit 202 to the liquid-vapor separation 18. This provides better temperature control in the liquid vapor separator 18 and will also provide a higher efficiency in splitting the propane and propylene from the butylenes and normal butane.

Figure 3:
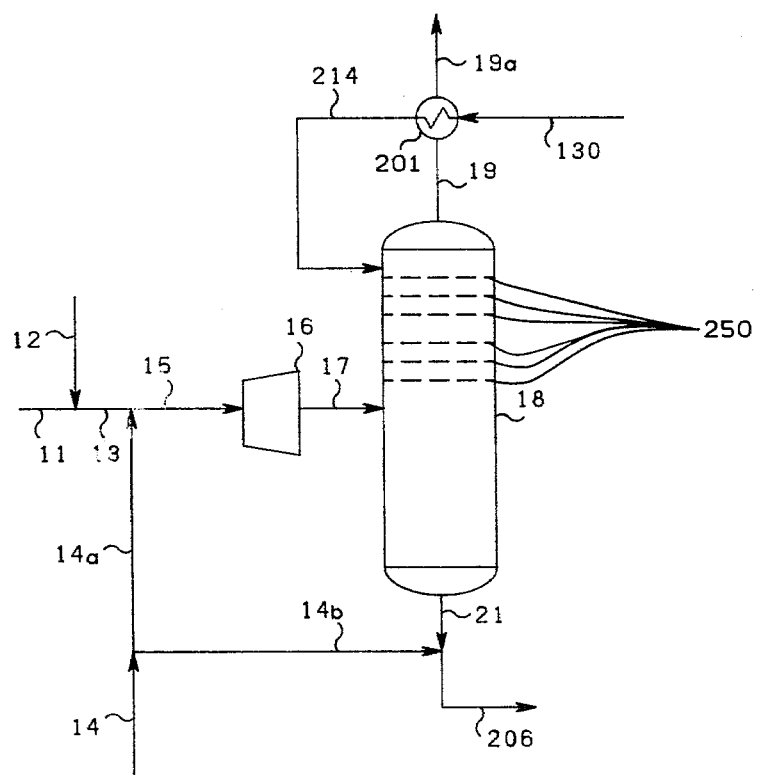
FIG. 3 is a diagrammatic illustration of a liquid-vapor separator having trays therein which can be incorporated in the alkylation process illustrated in FIG. 1.

A further variation of the alkylation process illustrated in FIG. 1 is illustrated in FIG. 3. Conventional liquid-vapor contact trays 250 are utilized in the upper section of the liquid-vapor separator 18. The reflux flowing through conduit means 130 and heat exchanger 201 is provided directly to the liquid-vapor separator 18 through conduit means 214. This system concentrates the propane and propylene in the overhead stream flowing through conduit means 19 and keeps the butylenes content in the overhead stream very low. The variation illustrated in FIG. 3 thus results in an improved separation between the propylene and the butylenes.

The invention has been illustrated in terms of a preferred embodiment as is illustrated in FIGS. 1-3. Conventional process equipment has been utilized. Other types of process equipment, which accomplishes the purpose of the process equipment illustrated in FIGS. 1-3, could be utilized if desired.

While the invention has been described in terms of the presently preferred embodiments, reasonable variations and modifications are possible by those skilled in the art, within the scope of the described invention and the appended claims.

That which is claimed is:

1. Apparatus comprising:

an olefin alkylation reactor means;

means for supplying a feed comprising at least one olefin, an acid catalyst, and at least one isoparaffin to said olefin alkylation reactor means;

a settler means;

means for withdrawing a reaction product comprising the alkylate of said at least one olefin, said acid catalyst and any unreacted portion of said at least one isoparaffin from said olefin alkylation reactor means and for supplying said reaction product as a feed to said settler means;

a stripping column means;

means for withdrawing a separated stream comprising the alkylate of said at least one olefin, any unreacted portion of said at least one isoparaffin and a reduced concentration of said acid catalyst, than was present in said reaction product, from said settler means and for supplying said separated stream as a feed to said stripping column means;

a first liquid-vapor separator means;

means for withdrawing a stripped stream comprising the alkylate of said at least one olefin and a reduced concentration of any unreacted portion of said at least one isoparaffin, than was present in said separated stream, from said stripping column means and for supplying said stripped stream to said first liquid-vapor separator means;

an isostripper means; and means for withdrawing an isostripper feed stream comprising the alkylate of said at least one olefin and a reduced concentration of any unreacted portion of said at least one isoparaffin, than was present in said stripped stream, from said first liquid-vapor separator means and for supplying said isostripper feed stream to said isostripper means.

2. Apparatus in accordance with claim 1 wherein said at least one olefin is butylenes and said olefin alkylation reactor means is a butylenes alkylation reactor means.

3. Apparatus in accordance with claim 2 additionally comprising:

a first expander means;

a second liquid-vapor separator means;

means for supplying a feed stream comprising propylene, butylenes, and said at least one isoparaffin through said first expander means to said second liquid-vapor separator means;

a propylene alkylation reactor means;

means for supplying an overhead product comprising propylene and at least a portion of said at least one isoparaffin from said second liquid-vapor separator means to said propylene alkylation reactor means; and means for supplying a bottoms product comprising butylenes and at least a portion of said at least one isoparaffin from said second liquid-vapor separator means to said butylenes alkylation reactor means.

4. Apparatus in accordance with claim 3 additionally comprising:

a heat exchanger means;

a second expander means;

means for withdrawing acid catalyst from said settler means and for passing the thus withdrawn acid catalyst through said heat exchanger means to said butylenes alkylation reactor means;

means for supplying said stripped stream through said second expander means and said heat exchanger means to thereby provide cooling for the acid catalyst flowing from said settler means to said butylenes alkylation reactor means.

5. Apparatus in accordance with claim 4 wherein said second liquid-vapor separator means contains liquid-vapor contact trays in the upper portion thereof.

6. Apparatus in accordance with claim 5 wherein said acid catalyst is hydrofluoric acid and said at least one isoparaffin is isobutane.

7. Apparatus in accordance with claim 2 additionally comprising:

an expander means;

a second liquid-vapor separator means;

means for supplying a feed stream comprising propylene, butylenes, and said at least one isoparaffin through said expander means to said second liquid-vapor separator means;

a propylene alkylation reactor means;

means for supplying an overhead product comprising propylene and at least a portion of said at least one isoparaffin from said second liquid-vapor separator means to said propylene alkylation reactor means;

a hydrofluorination reactor means;

means for supplying a bottoms product comprising butylenes and at least a portion of said at least one isoparaffin from said second liquid-vapor separator means to said hydrofluorination reactor means;

means for supplying said acid catalyst to said hydrofluorination reactor means; and means for withdrawing a fluorinated reaction product comprising butylfluorides and at least a portion of said at least one isoparaffin from said hydrofluorination reactor and for supplying said fluorination reaction product to said butylenes alkylation reactor means.

8. Apparatus in accordance with claim 7 wherein said acid catalyst is hydrofluoric acid and said at least one isoparaffin is isobutane.

9. Apparatus comprising:

an expander means;

a liquid-vapor separator means;

means for supplying a feed stream comprising propylene, butylenes, and at least one isoparaffin through said expander means to said liquid-vapor separator means;

a propylene alkylation reactor means;

means for supplying an overhead product comprising propylene and at least a portion of said at least one isoparaffin from said liquid-vapor separator means to said propylene alkylation reactor;

a butylenes alkylation reactor means; and means for supplying a bottoms product comprising butylenes and at least a portion of said at least one isoparaffin from said liquid-vapor separator means to said butylenes alkylation reactor means.

10. Apparatus in accordance with claim 9 wherein said liquid-vapor separator means contains liquid-vapor contact trays in the upper portion thereof.

11. Apparatus in accordance with claim 10 wherein said at least one isoparaffin is isobutane.

12. Apparatus comprising:

an olefin alkylation reactor means;

means for supplying a feed comprising at least one olefin, an acid catalyst, and at least one isoparaffin to said olefin alkylation reactor means;

a settler means;

means for withdrawing a reaction product comprising the alkylate of said at least one olefin, said acid catalyst and any unreacted portion of said at least one isoparaffin from said olefin alkylation reactor means and for supplying said reaction product as a feed to said settler means;

a stripping column means;

means for withdrawing a separated stream comprising the alkylate of said at least one olefin, any unreacted portion of said at least one isoparaffin and a reduced concentration of said acid catalyst, than was present in said reaction product, from said settler means and for supplying said separated stream as a feed to said stripping column means;

an expander means;

a heat exchanger means;

means for supplying the acid catalyst separated from said reactor product in said settler means from said settler means through said heat exchanger means to said olefin alkylation reactor means; and means for supplying a stripped stream comprising the alkylate of said at least one olefin and a reduced concentration of the unreacted portion of said at least one isoparaffin, than was present in said separated stream from said stripping column means through said expander means and said heat exchanger means to thereby provide cooling for the acid catalyst flowing from said settler means to said olefin alkylation reactor means.

13. Apparatus in accordance with claim 12 wherein said at least one olefin is butylenes, said acid catalyst is hydrofluoric acid and said at least one isoparaffin is isobutane.

14. An alkylation process comprising the steps of:
alkylating at least one olefin and at least one isoparaffin in the presence of an acid catalyst to thereby produce a reaction product comprising the alkylate of said at least one olefin, said acid catalyst and any unreacted portion of said at least one isoparaffin;
phase separating a substantial portion of said acid catalyst from said reaction product to thereby produce a separated product comprising the alkylate of said at least one olefin, any unreacted portion of said at least one isoparaffin and a reduced concentration of said acid catalyst, than was present in said reaction product;
stripping a substantial portion of said acid catalyst remaining in said separated product and at least a portion of any unreacted portion of said at least one isoparaffin from said separated product to thereby produce a stripped product;
phase separating said stripped product to thereby provide a phase separated product having a reduced concentration of any unreacted portion of said at least one isoparaffin than was present in said stripped product; and
stripping the remaining portion of said at least one isoparaffin from said phase separated product to thereby provide a substantially pure alkylate of said at least one olefin.

15. A process in accordance with claim 14 wherein said at least one olefin is butylenes.

16. A process in accordance with claim 15 comprising the additional steps of:
expanding a feed stream comprising propylene, butylenes, and at least one isoparaffin to thereby provide an expanded feed stream having a vapor phase and a liquid phase;
phase separating said expanded feed stream, without the addition of heat, to thereby provide an overhead stream comprising propylene and at least a portion of said at least one isoparaffin and a bottoms stream comprising butylenes and at least a portion of said at least one isoparaffin; and
alkylating said propylene and said butylenes with said at least one isoparaffin in separate alkylation reactions.

17. A process in accordance with claim 5 additionally comprising the step of utilizing said stripped stream to cool the acid catalyst utilized in the alkylation of said butylenes with said at least one isoparaffin.

18. A process in accordance with claim 16 additionally comprising hydrofluorinating the butylenes prior to the alkylation of said butylenes with said at least one isoparaffin.

19. A process in accordance with claim 18 wherein said acid catalyst is hydrofluoric acid and said at least one isoparaffin is isobutane.

20. An alkylation process comprising the steps of:
expanding a feed stream comprising propylene, butylenes, and at least one isoparaffin to thereby provide an expanded feed stream having a vapor phase and a liquid phase;
phase separating said expanded feed stream, without the addition of heat, to thereby provide an overhead product comprising propylene and at least a portion of said at least one isoparaffin and a bottoms product comprising butylenes and at least a portion of said at least one isoparaffin;
alkylating said propylene and said at least one isoparaffin in the presence of an acid catalyst; and
alkylating said butylenes and said at least one isoparaffin in the presence of said acid catalyst.

21. A process for cooling the acid catalyst in an olefin alkylation reactor comprising the steps of:
alkylating at least one olefin with at least one isoparaffin in the presence of an acid catalyst to thereby produce a reaction product comprising the alkylate of said at least one olefin, and acid catalyst and the unreacted portion of said at least one isoparaffin;
phase separating a substantial portion of said acid catalyst from said reaction product to thereby produce a separated product comprising the alkylate of said at least one olefin, any unreacted portion of said at least one isoparaffin and a reduced concentration of said acid catalyst, than was present in said reaction product;
stripping at least a portion of said acid catalyst remaining in said separated product and at least a portion of any unreacted portion of said at least one isoparaffin from said separated product to thereby produce a stripped stream; and
utilizing said stripped stream to cool the acid catalyst utilized in the alkylation of said at least one olefin with said at least one isoparaffin.

* * * * *